United States Patent
Sekido

(10) Patent No.: US 11,962,103 B2
(45) Date of Patent: Apr. 16, 2024

(54) CABLE CONNECTION STRUCTURE, ENDOSCOPE, AND METHOD OF MANUFACTURING CABLE CONNECTION STRUCTURE

(71) Applicant: OLYMPUS CORPORATION, Tokyo (JP)

(72) Inventor: Takanori Sekido, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 622 days.

(21) Appl. No.: 17/137,712

(22) Filed: Dec. 30, 2020

(65) Prior Publication Data

US 2021/0119357 A1   Apr. 22, 2021

Related U.S. Application Data

(63) Continuation of application No. PCT/JP2018/026080, filed on Jul. 10, 2018.

(51) Int. Cl.
*H01R 12/53*   (2011.01)
*A61B 1/00*   (2006.01)
*H01R 43/02*   (2006.01)

(52) U.S. Cl.
CPC ............ *H01R 12/53* (2013.01); *A61B 1/0011* (2013.01); *A61B 1/00114* (2013.01);
(Continued)

(58) Field of Classification Search
CPC ............ H01R 12/53; H01R 43/0249; H01R 43/0263; A61B 1/0011; A61B 1/00114; A61B 1/00124
(Continued)

(56) References Cited

U.S. PATENT DOCUMENTS 5,281,762 A * 1/1994 Long .................... H01R 12/598
  29/857
5,347,711 A * 9/1994 Wheatcraft ............ H05K 3/301
  29/843
(Continued)

FOREIGN PATENT DOCUMENTS

JP   H11-509030 A   8/1999
JP   2011-204572 A   10/2011
(Continued)

OTHER PUBLICATIONS

International Search Report dated Sep. 25, 2018 issued in PCT/JP2018/026080.

*Primary Examiner* — Anatoly Vortman
(74) *Attorney, Agent, or Firm* — Scully, Scott, Murphy & Presser, P.C.

(57) ABSTRACT

A cable connection structure includes: cables, each including a jacket and a core wire exposed at an end portion by removing the jacket; a first fixing member configured to fix distal end portions of exposed core wires while holding the cables at predetermined intervals; a second fixing member configured to fix proximal end portions of the exposed core wires while holding the cables at predetermined intervals; and a substrate including a core wire connection electrode configured to electrically connect the core wire at a position between the first fixing member and the second fixing member, wherein the first fixing member and the second fixing member are different members.

16 Claims, 7 Drawing Sheets

(52) U.S. Cl.
CPC ..... *A61B 1/00124* (2013.01); *H01R 43/0249* (2013.01); *H01R 43/0263* (2013.01)

(58) Field of Classification Search
USPC .......................................................... 174/251
See application file for complete search history.

(56) References Cited

U.S. PATENT DOCUMENTS

| | | | |
|---|---|---|---|
| 5,710,393 A | 1/1998 | Smith et al. | |
| 5,781,991 A * | 7/1998 | Papon | H01R 43/0256 29/828 |
| 5,815,916 A * | 10/1998 | Luc | H01R 43/0256 29/33 M |
| 7,973,239 B2 * | 7/2011 | Koyama | H01R 9/0506 174/78 |
| 8,210,867 B2 * | 7/2012 | Kojima | H01R 9/0515 439/83 |
| 8,889,996 B2 * | 11/2014 | Yamada | H05K 1/111 174/251 |
| 9,520,212 B2 * | 12/2016 | Sekido | A61B 1/00124 |
| 2009/0101408 A1 | 4/2009 | Koyama et al. | |
| 2010/0210120 A1 * | 8/2010 | Maruishi | H01R 12/79 439/77 |
| 2011/0244723 A1 | 10/2011 | Kojima | |
| 2011/0306235 A1 * | 12/2011 | Tanaka | H01R 4/027 439/578 |
| 2013/0005181 A1 * | 1/2013 | Yamada | H01R 9/0515 439/578 |
| 2014/0144697 A1 * | 5/2014 | Sekido | A61B 1/00124 29/428 |
| 2015/0011891 A1 * | 1/2015 | Yamada | H01R 13/655 600/459 |
| 2016/0093991 A1 * | 3/2016 | Kobayashi | H01R 12/53 439/579 |
| 2017/0301433 A1 * | 10/2017 | Sekido | H01R 43/0256 |
| 2018/0132704 A1 | 5/2018 | Yamada et al. | |
| 2019/0296537 A1 * | 9/2019 | Mikami | H01R 12/53 |
| 2021/0226396 A1 * | 7/2021 | Sekido | H01R 12/62 |

FOREIGN PATENT DOCUMENTS

| | | |
|---|---|---|
| JP | 2011-258460 A | 12/2011 |
| JP | 5510090 B2 | 6/2014 |
| WO | 96/37018 A1 | 11/1996 |
| WO | 2008/082018 A1 | 7/2008 |
| WO | 2010/070853 A1 | 6/2010 |
| WO | 2017/013745 A1 | 1/2017 |

* cited by examiner

CABLE CONNECTION STRUCTURE, ENDOSCOPE, AND METHOD OF MANUFACTURING CABLE CONNECTION STRUCTURE

This application is a continuation of International Application No. PCT/JP2018/026080, filed on Jul. 10, 2018, the entire contents of which are incorporated herein by reference.

BACKGROUND

The present disclosure relates to a cable connection structure, an endoscope, and a method of manufacturing a cable connection structure.

A known endoscope has a configuration with a flexible and elongated insertion section including, at a distal end thereof, an imaging device, and when the insertion section is inserted into a subject such as a patient, image data of the inside of the subject is acquired by the imaging device at the distal end portion so as to be transmitted to an external information processing device. In order to transmit/receive drive power, clock signals, or the like, in addition to the image data, a plurality of cables is utilized, and the plurality of cables is connected to a substrate of the imaging device.

There has been a proposed technique for performing cable connection to electrodes arranged with a narrow pitch while suppressing cable misalignment (refer to JP 5510090 B).

SUMMARY

According to one aspect of the present disclosure, there is provided a cable connection structure including: cables, each including a jacket and a core wire exposed at an end portion by removing the jacket; a first fixing member configured to fix distal end portions of exposed core wires while holding the cables at predetermined intervals; a second fixing member configured to fix proximal end portions of the exposed core wires while holding the cables at predetermined intervals; and a substrate including a core wire connection electrode configured to electrically connect the core wire at a position between the first fixing member and the second fixing member, wherein the first fixing member and the second fixing member are different members.

The above and other features, advantages and technical and industrial significance of this disclosure will be better understood by reading the following detailed description of embodiments of the disclosure, when considered in connection with the accompanying drawings.

DETAILED DESCRIPTION

Hereinafter, an endoscope system including a cable connection structure will be described according to embodiments (hereinafter, referred to as "embodiment(s)"). In addition, the present disclosure is not limited by the embodiment. Furthermore, each of drawings referred to in the following description is merely an example schematically illustrating shapes, size, and positional relationships to the degree that makes the present disclosure understandable. That is, the present disclosure is not limited only to the shapes, the size and the positional relationships illustrated in each of the drawings. Furthermore, dimensions and ratios may be mutually different in individual drawings.

Figure 1:
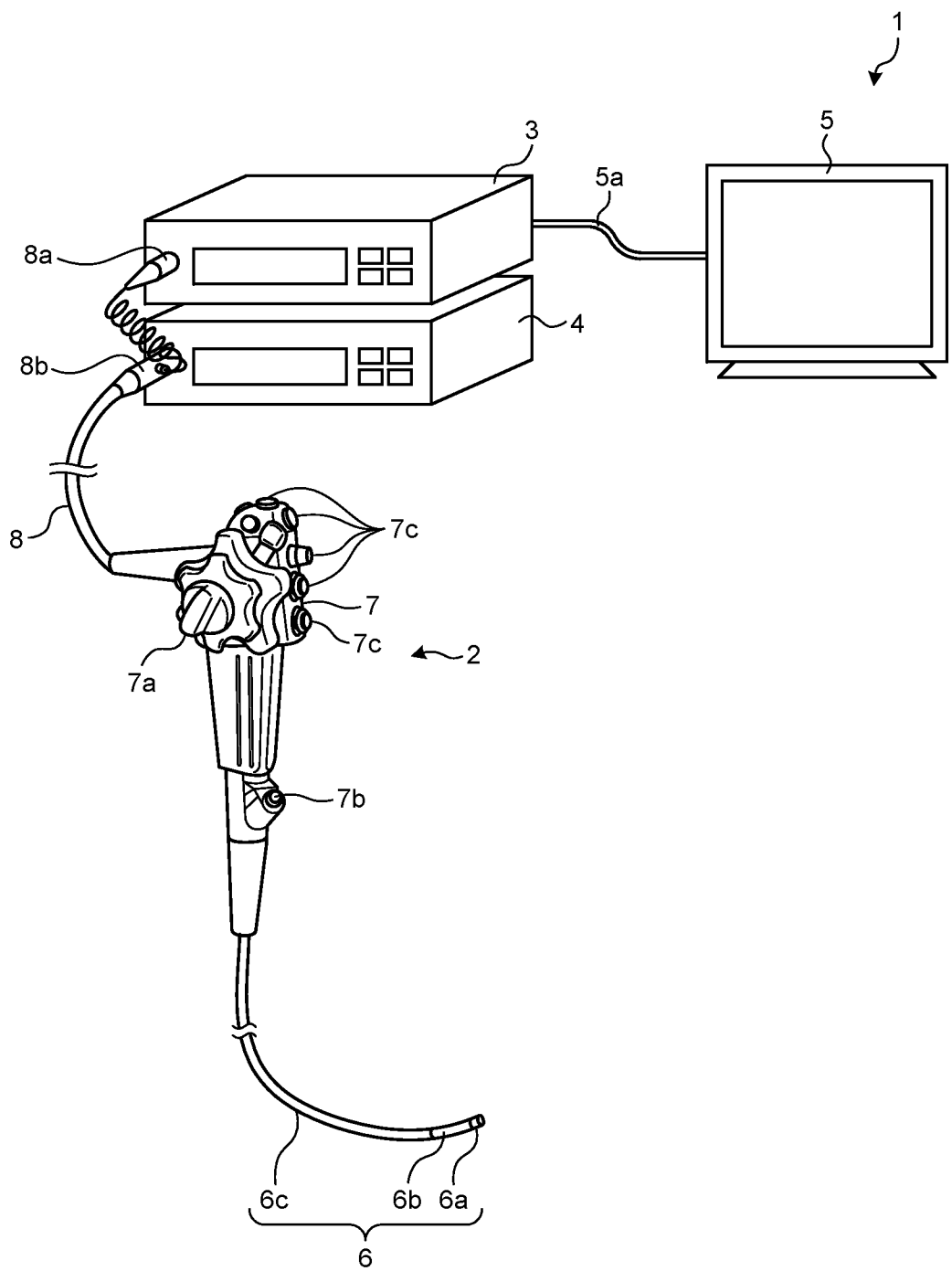
FIG. 1 is a view schematically illustrating an overall configuration of an endoscope system according to a first embodiment.

FIG. 1 is a view schematically illustrating an overall configuration of an endoscope system 1 according to a first embodiment. As illustrated in FIG. 1, an endoscope system 1 includes an endoscope 2 that is introduced into a subject and captures an image inside the body of a subject and generates an image signal of the interior of the subject, an information processing device 3 that performs predetermined image processing on the image signal captured by the endoscope 2 and controls each of portions of the endoscope system 1, a light source device 4 that generates illumination light for the endoscope 2, and a display device 5 that displays an image of the image signal after undergoing image processing performed by the information processing device 3.

The endoscope 2 includes an insertion section 6 that is inserted into the subject, an operating unit 7 that is arranged on a proximal end side of the insertion section 6 and gripped by a surgeon, and a universal cord 8 that has flexibility and extends from the operating unit 7.

The insertion section 6 includes a light guide using an illumination fiber, an electric cable, an optical fiber, etc. The insertion section 6 includes a distal end portion 6a including an imaging device described below, a bending portion 6b that is a bendable portion formed with a plurality of bending pieces, and a flexible tube portion 6c that is flexible and provided on a proximal end side of the bending portion 6b. The distal end portion 6a includes an illumination unit that illuminates an inside of the subject through an illumination lens, an observation unit that captures an internal image of the subject, an aperture portion communicating with a treatment tool channel, and an air/water feeding nozzle (not illustrated).

The operating unit 7 includes a bending knob 7a used to bend the bending portion 6b in up-down and left-right directions, a treatment tool insertion section 7b being a section through which treatment tools such as biological forceps and a laser knife are inserted into the body cavity of the subject, and a plurality of switching sections 7c used to operate peripheral equipment such as the information processing device 3, the light source device 4, an air feeding device, a water feeding device, and a gas feeding device. A treatment tool inserted from the treatment tool insertion section 7b passes through an internal treatment tool channel and comes out from the aperture portion of the distal end of the insertion section 6.

The universal cord 8 includes a light guide formed of a lighting fiber, a cable, etc. The universal cord 8 is branched at a proximal end. One end portion of the branched section is a connector 8a, and the other proximal end is a connector 8b. The connector 8a is removably attached to the connector of the information processing device 3. The connector 8b is removably attached to the light source device 4. The universal cord 8 transmits illumination light emitted from the light source device 4 to the distal end portion 6a via the connector 8b and the light guide formed with the illumination fiber. Moreover, the universal cord 8 transmits an image signal captured by an imaging device to be described below to the information processing device 3 via the cable and the connector 8a.

The information processing device 3 performs predetermined image processing on the image signal output from the connector 8a, while controlling the whole endoscope system 1.

The light source device 4 includes a light source that emits light, a condenser lens, etc. Under the control of the information processing device 3, the light source device 4 emits light from the light source and supplies the light to the endoscope 2 connected via the connector 8b and the light guide formed with the illumination fiber of the universal cord 8, as illumination light supplied to the inside of the subject as an object.

The display device 5 includes a display using liquid crystal or organic electro luminescence (EL). The display device 5 displays, via a video cable 5a, various types of information including an image that has undergone predetermined image processing performed by the information processing device 3. With this configuration, the surgeon may perform observation of a desired position inside the subject and diagnosis of the symptoms by operating the endoscope 2 while viewing an image (in-vivo image) displayed by the display device 5.

Figure 2:
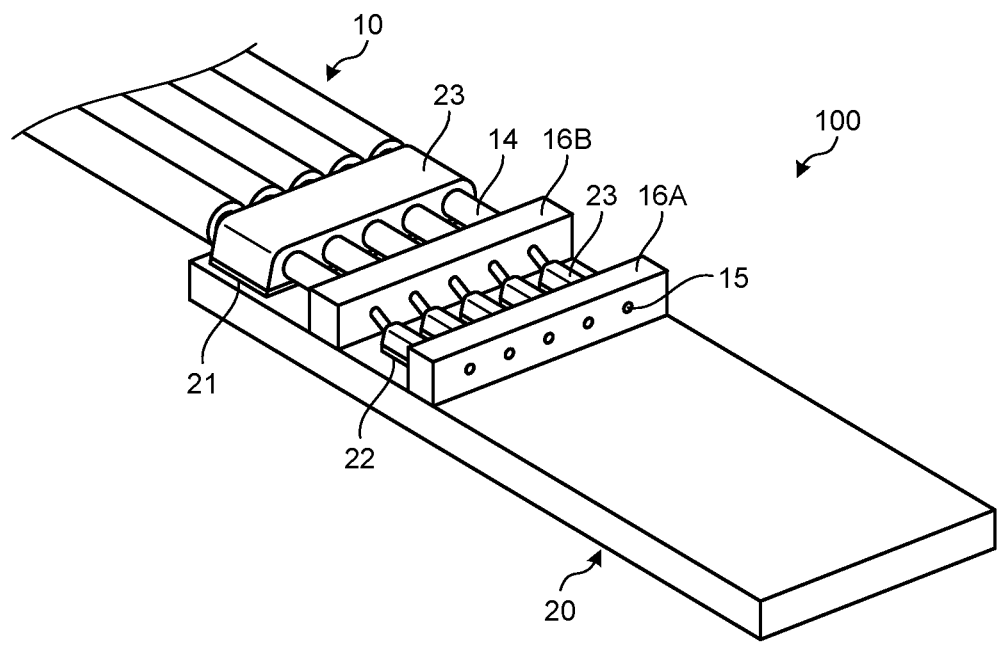
FIG. 2 is a perspective view of a cable connection structure used in an endoscope according to the first embodiment.
Figure 3:
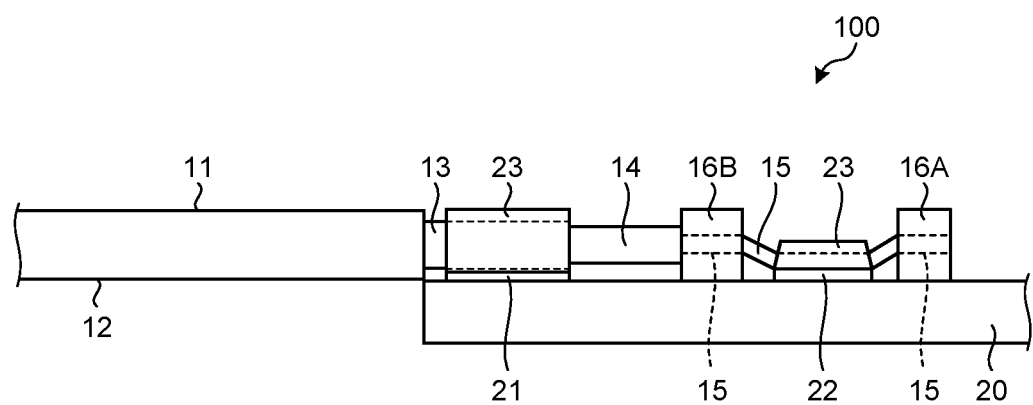
FIG. 3 is a side view of the cable connection structure of FIG. 2 as seen in the cable extending direction.
Figure 4:
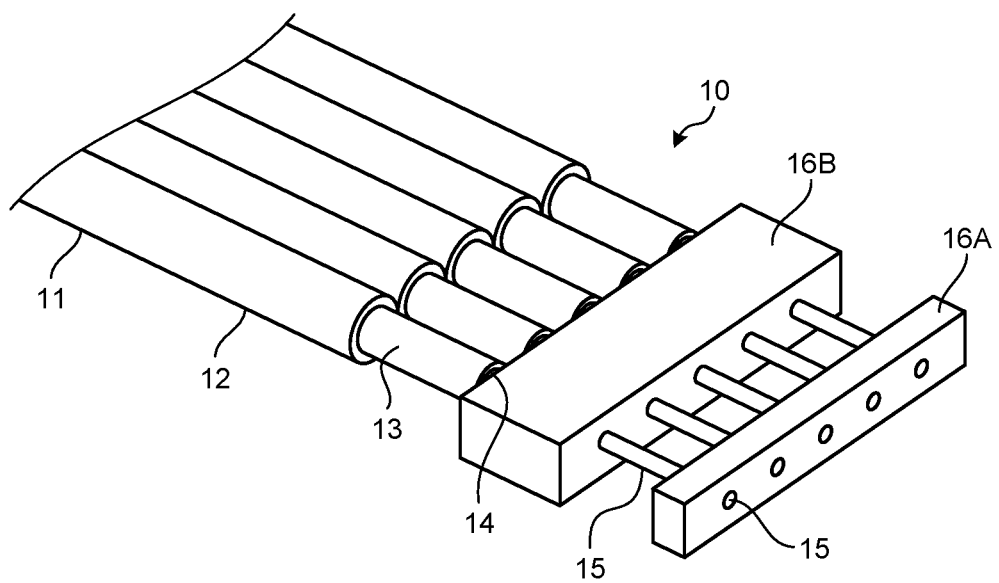
FIG. 4 is a perspective view of a cable assembly used for the cable connection structure of FIG. 2.

Next, the cable connection structure 100 used in the endoscope system 1 will be described in detail. FIG. 2 is a perspective view of a cable connection structure 100 used in the endoscope 2 according to the first embodiment. FIG. 3 is a side view of the cable connection structure 100 of FIG. 2 as seen in the cable extending direction. FIG. 4 is a perspective view of a cable assembly 10 used for the cable connection structure 100 of FIG. 2.

The cable connection structure 100 includes the cable assembly 10 and a substrate 20.

The cable assembly 10 includes a plurality of coaxial cables 11, a first fixing member 16A and a second fixing member 16B adapted to fix a second portion (core wire 15) and a third portion (core wire 15), respectively, of the plurality of coaxial cables 11 while holding the cables at predetermined intervals.

The coaxial cable 11 is formed with a core wire 15, a dielectric 14 as a covering around the core wire 15, a shield 13 as a covering around the dielectric 14, and a jacket 12 as a covering around the shield 13. In the coaxial cable 11, the jacket 12, the shield 13, and the dielectric 14 are removed so that the core wire 15, the dielectric 14, and the shield 13 are revealed stepwise.

The first fixing member 16A and the second fixing member 16B are each formed of an insulating resin such as an ultraviolet curable resin.

The substrate 20 is equipped with a core wire connection electrode 22 that connects the core wire 15 ("first portion" 15 of the coaxial cable 11), and a shield connection electrode 21 that connects the shield 13. The core wire 15 and the shield 13 are electrically connected to the core wire connection electrode 22 and the shield connection electrode 21 by solder 23. The solder 23 may be another conductive material such as a conductive adhesive.

Next, a method of manufacturing the cable assembly 10 will be described with reference to the drawings. FIGS. 5A to 5F are views illustrating a method of manufacturing the cable assembly 10 of FIG. 2.

Figure 5A:
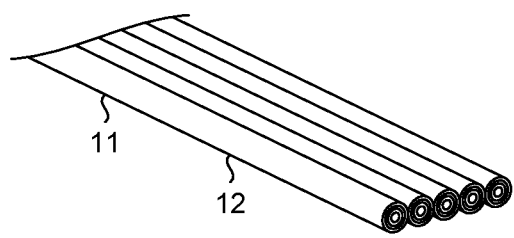
FIGS. 5A to 5F are views illustrating a method of manufacturing the cable assembly of FIG. 2.

First, as illustrated in FIG. 5A, the plurality of coaxial cables 11 is held at predetermined intervals by a jig (not illustrated). The coaxial cables 11 are held with a jig at two locations, the distal end side and the proximal end side. The jig used here is a member having a groove that fits a pitch interval of the coaxial cable 11. By setting the coaxial cable 11 into the groove, it is possible to adjust the intervals of the coaxial cables 11.

Figure 5B:
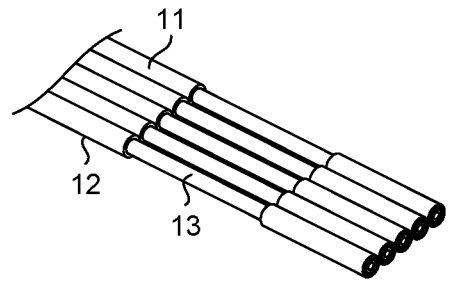

Next, as illustrated in FIG. 5B, the jacket 12 is removed by laser processing or the like to reveal the shield 13. The jackets 12 at both ends of the coaxial cable 11 held by the jig are left unremoved.

Figure 5C:
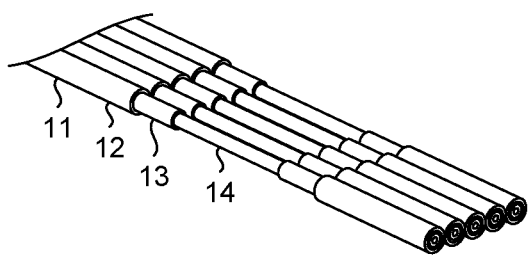

As illustrated in FIG. 5C, the shield 13 is removed by laser processing or the like to reveal the dielectric 14 while leaving at least the shield 13 on the proximal end side. Although FIG. 5C is a case where the removal of the shield 13 is performed so as to leave the shield 13 unremoved at both ends, it is allowable to also remove the distal end-side shield 13 as long as the shield 13 connected to the shield connection electrode 21 of the substrate 20 may be left unremoved on the proximal end side (coaxial cable 11 extending direction side).

Figure 5D:
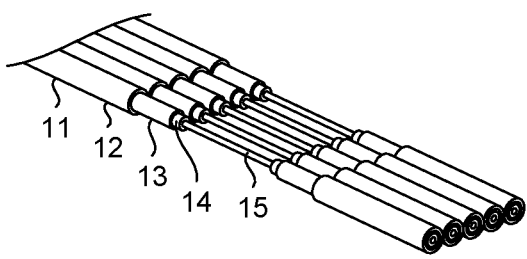

As illustrated in FIG. 5D, the core wire 15 is revealed by partially removing the dielectric 14 using laser processing or the like in a state of leaving at least a part of the dielectric 14 revealed on the proximal end side unremoved. The length of the dielectric 14 to leave unremoved may be short. Still, by leaving the dielectric 14 unremoved on the proximal end side, it would be possible to prevent a short circuit between the shield 13 and the core wire 15. Although FIG. 5D is a case where the removal of the dielectric 14 is performed so as to leave the dielectric 14 unremoved at both ends, the dielectric 14 on the distal end side may be removed.

Figure 5E:
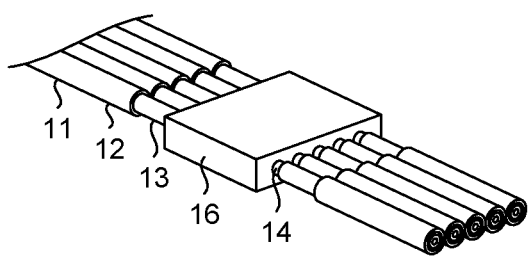

As illustrated in FIG. 5E, an ultraviolet curable resin or the like is used to seal the surroundings of the revealed core wire 15, thereby forming a resin fixing portion 16. The resin fixing portion 16 may be formed by a method in which an uncured ultraviolet curable resin is applied around the core wire 15 or injected into a mold installed around the core wire 15 and cured.

Figure 5F:
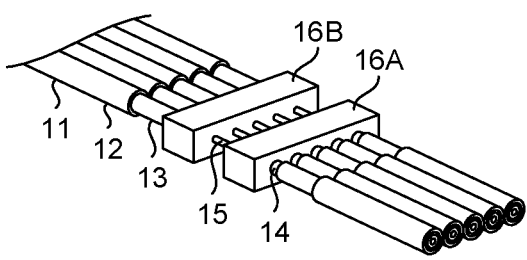

As illustrated in FIG. 5F, the resin fixing portion 16 is partially removed and then divided into a distal end side and a proximal end side to form a first fixing member 16A and a second fixing member 16B, respectively. At the removal of the resin fixing portion 16, the resin alone is removed to reveal the core wire 15 between the first fixing member 16A and the second fixing member 16B. The revealed core wire 15 will be connected to the core wire connection electrode 22 of the substrate 20.

Thereafter, the first fixing member 16A on the distal end side is cut perpendicularly to the extending direction of the coaxial cable 11 using laser processing or the like, thereby enabling manufacture of the cable assembly 10.

Furthermore, the cable connection structure 100 is manufactured by connecting, by the solder 23, the revealed shield 13 and core wire 15 of the obtained cable assembly 10 respectively to the shield connection electrode 21 and the core wire connection electrode 22 of the substrate 20.

According to the cable connection structure 100 of the first embodiment, it is possible to remove the jacket 12, the shield 13, and the dielectric 14 in a state where both ends of the plurality of coaxial cables 11 are fixed with jigs, making it possible to collectively to process the plurality of coaxial cables 11. Furthermore, fixing both ends of the plurality of coaxial cables 11 with jigs enables stabled postures of the plurality of coaxial cables 11. With this advantage, when the coaxial cables are processed by laser processing, it is possible to perform highly accurate alignment of the coaxial cables with respect to the focal position of the laser, leading to successful processing. As a result, the work may be easily performed. Furthermore, both ends of the plurality of coaxial cables 11 are held and fixed at predetermined intervals by the first fixing member 16A and the second fixing member 16B. This makes it possible to improve the pitch accuracy of the coaxial cables 11, leading to the reduction of the occurrence of short circuits even at a narrow pitch.

In the cable connection structure 100 of the first embodiment, the first fixing member 16A and the second fixing member 16B are not connected to the substrate 20. However, these members may be fixed to the substrate 20 with an adhesive or the like. Using a configuration in which the first fixing member 16A and the second fixing member 16B are fixed to the substrate 20, it is possible to prevent breakage of a connection portion even when the coaxial cable 11 or the like is subjected to the stress due to application of excessive force.

Although the above-described first embodiment is an exemplary case of the cable connection structure 100 using the cable assembly 10 formed with a plurality of coaxial cables 11, it is also possible to obtain similar effects by using a cable assembly formed of a single wire (simple wire) cable in which the core wire is covered with a jacket. In the case of using a single wire cable, it is possible to remove the jacket at the end to reveal the core wire, and fix the distal end portion of the revealed core wire by using the first fixing member, while fixing the proximal end portion by using the second fixing member. With this configuration, it is also possible to improve the cable pitch accuracy, leading to the reduction of the occurrence of short circuits even at a narrow pitch.

Furthermore, similar effects may be obtained by using a cable assembly combining a coaxial cable and a single wire cable.

Figure 6:
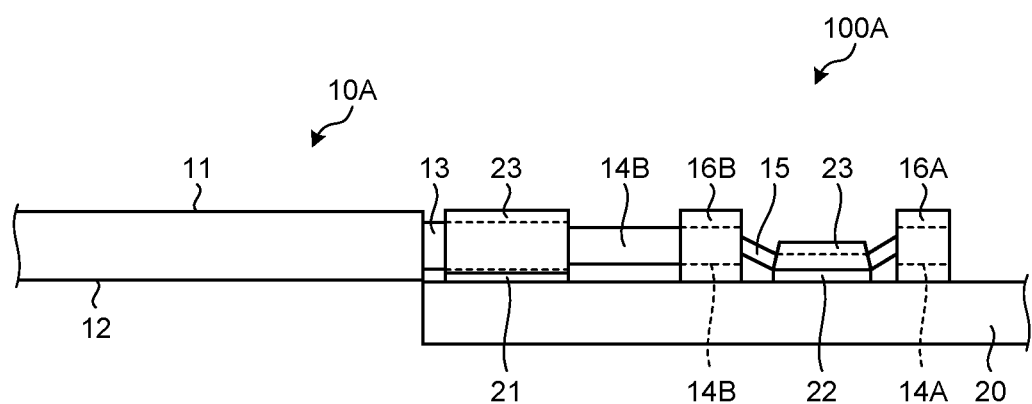
FIG. 6 is a side view of a cable connection structure according to a second embodiment, as seen in the cable extending direction.

In a second embodiment, the first fixing member 16A and the second fixing member 16B are formed around the revealed dielectric 14. FIG. 6 is a side view of a cable connection structure 100A according to the second embodiment, as seen in a cable extending direction.

The cable connection structure 100A of the second embodiment includes a cable assembly 10A and a substrate 20. In the cable assembly 10A, the first fixing member 16A and the second fixing member 16B are formed for the purpose of providing a covering around the revealed dielectric 14 (a second portion 14A of the cable 11 is fixed by the first fixing member 16A and a second portion 14B of the cable 11 is fixed by the second fixing member 16B, each of the second and third portions in FIG. 6 being the revealed dielectric). When the material of the dielectric 14 has low adhesiveness to the resin, it is preferable to apply surface treatment on the dielectric 14 in order to improve the adhesiveness.

Next, a method of manufacturing the cable assembly 10A will be described with reference to the figures. FIGS. 7A to 7E are views illustrating a method of manufacturing the cable assembly 10A of FIG. 6.

Figure 7A:
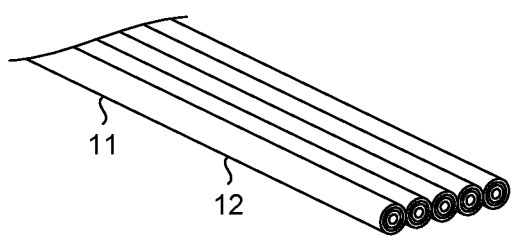
FIGS. 7A to 7E are views illustrating a method of manufacturing the cable assembly of FIG. 6.
Figure 7B:
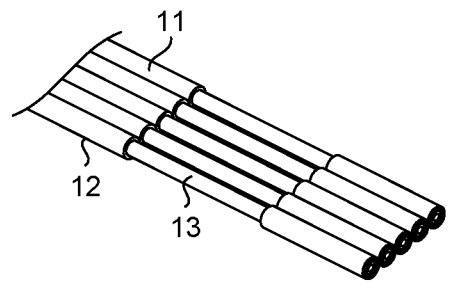
Figure 7C:
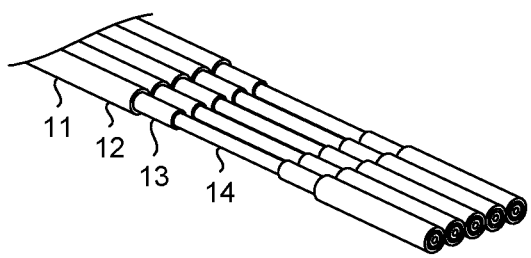
Figure 7D:
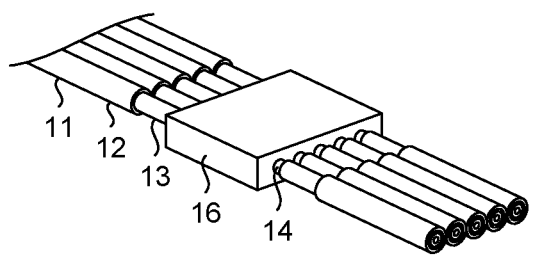

Processes of FIGS. 7A to 7C are performed similarly to the processes of FIGS. 5A to 5C of the first embodiment. Thereafter, as illustrated in FIG. 7D, an ultraviolet curable resin or the like is used to seal around the revealed dielectric 14, thereby forming a resin fixing portion 16.

Figure 7E:
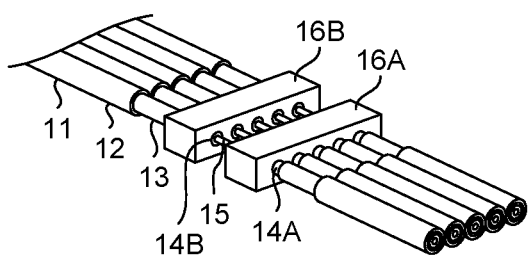

As illustrated in FIG. 7E, the resin fixing portion 16 is partially removed and then divided into a distal end side and a proximal end side to form a first fixing member 16A and a second fixing member 16B, respectively. At the removal of the resin fixing portion 16, the resin and the dielectric 14 are removed to reveal the core wire 15 between the first fixing member 16A and the second fixing member 16B. The revealed core wire 15 will be connected to the core wire connection electrode 22 of the substrate 20. In the cable connection structure 100A of the second embodiment, the first fixing member 16A provides a covering around a first dielectric 14A existing independently on the distal end side, while the second fixing member 16B provides a covering around a second dielectric 14B revealed on the proximal end side.

Similarly to the first embodiment, the cable connection structure 100A of the second embodiment enables the removal of the jacket 12, the shield 13, and the dielectric 14 in a state where both ends of the plurality of coaxial cables 11 are fixed with jigs, making it possible to collectively process the plurality of coaxial cables 11. Furthermore, fixing both ends of the plurality of coaxial cables 11 with jigs enables stabled postures of the plurality of coaxial cables 11. With this advantage, when the coaxial cables are processed by laser processing, it is possible to perform highly accurate alignment of the coaxial cables with respect to the focal position of the laser, leading to successful processing. As a result, the work may be easily performed. Furthermore, both ends of the plurality of coaxial cables 11 are held and fixed at predetermined intervals by the first fixing member 16A and the second fixing member 16B. This makes it possible to improve the pitch accuracy of the coaxial cables 11, leading to the reduction of the occurrence of short circuits even at a narrow pitch.

Figure 8:
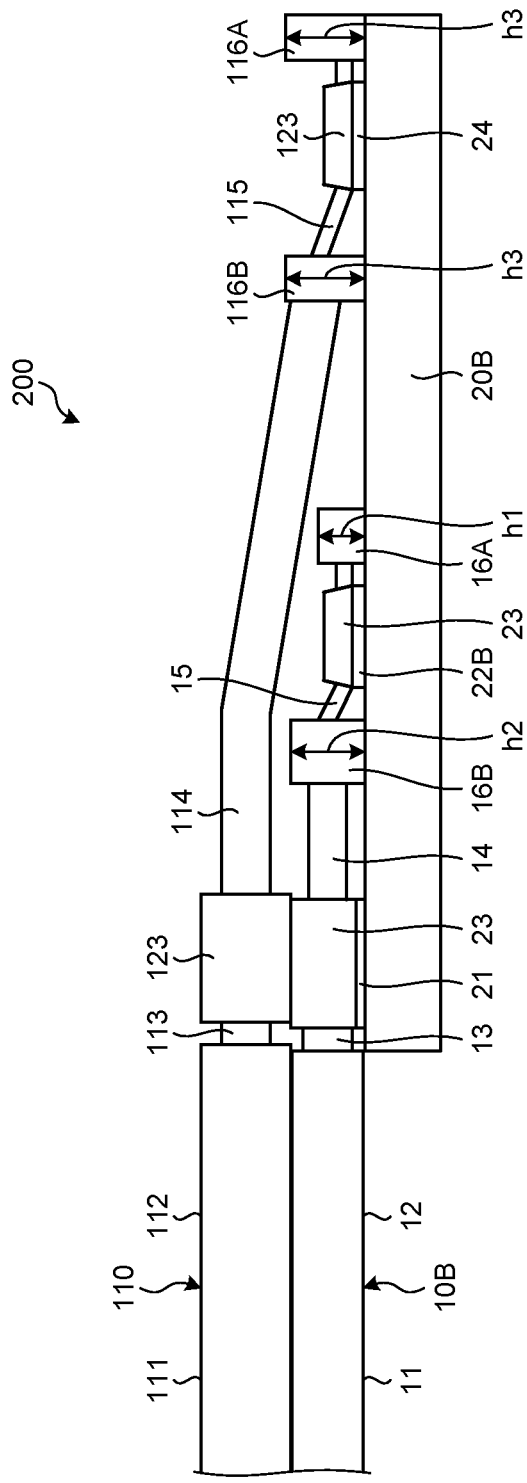
FIG. 8 is a side view of a cable connection structure according to a third embodiment.

In a third embodiment, cable assemblies are stacked in two stages of upper and lower stages and connected to the substrate. FIG. 8 is a side view of a cable connection structure 200 according to the third embodiment, as seen in the cable extending direction.

The cable connection structure 200 of the third embodiment includes a lower cable assembly 10B, an upper cable assembly 110, and a substrate 20B.

The lower cable assembly 10B has a structure similar to the structure of the cable assembly 10 of the first embodiment, and the revealed shield 13 is electrically connected to the shield connection electrode 21 by solder 23. Furthermore, the core wire 15 revealed between the first fixing member 16A and the second fixing member 16B is connected to a lower core wire connection electrode 22B by the solder 23.

The upper cable assembly 110 includes a plurality of coaxial cables 111, a first fixing member 116A and a second fixing member 116B adapted to fix the plurality of coaxial cables 111 while holding the cables at predetermined intervals.

Similarly to the coaxial cable 11, the coaxial cable 111 is constructed from a core wire 115, a dielectric 114 as a covering around the core wire 115, a shield 113 as a covering around the dielectric 114, and a jacket 112 as a covering around the shield 113. In the coaxial cable 111, the jacket 112, the shield 113, and the dielectric 114 are removed so that the core wire 115, the dielectric 114, and the shield 113 are revealed stepwise.

The revealed shield 113 of the upper cable assembly 110 is electrically connected, by solder 123, to the shield connection electrode 21 via the shield 13 and the solder 23 of the lower cable assembly 10B. Furthermore, the core wire 115 revealed between the first fixing member 116A and the second fixing member 116B is connected to an upper core wire connection electrode 24 by the solder 123.

As illustrated in FIG. 8, the proximal end side portion of the upper cable assembly 110 with respect to the second fixing member 116B is arranged above the lower cable assembly 10B. Furthermore, the upper core wire connection electrode 24 that connects the core wire of the upper cable assembly 110 is arranged in a state of being more separated from the shield connection electrode 21, compared to from the lower core wire connection electrode 22B that connects the core wire of the lower cable assembly 10B.

Furthermore, in the cable connection structure 200, in order to prevent interference between the upper cable assembly 110 and the lower cable assembly 10B, a height h3 of the first fixing member 116A and the second fixing member 116B of the upper cable assembly 110 is formed to be higher than a height h1 of the first fixing member 16A and a height h2 of the second fixing member 16B of the lower cable assembly 10B.

Furthermore, in order to prevent application of the load to the electric wire 11 due to the bending of the electric wire 11, the height h1 of the first fixing member 16A of the lower cable assembly 10B is desirably formed to be lower than the height H2 of the second fixing member 16B of the lower cable assembly 10B.

The height h1 of the first fixing member 16A and the height h2 of the second fixing member 16B of the lower cable assembly 10B may be the same.

The cable connection structure 200 according to the third embodiment has effects similar to the effects of the first embodiment. In addition, since the cables having a double stage structure including upper and lower stages are connected to the substrate, it is possible to reduce the mounting area. Accordingly, when the cable connection structure 200 is used for an endoscope or the like, it is possible to miniaturize the endoscope or the like.

According to the present disclosure, there are advantageous effects of enabling holding the cables at predetermined intervals without the need for complicated work, and reducing the possibility of short circuit even when the pitch is narrow.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable connection structure comprising:
    a plurality of cables, each including:
        a jacket; and
        a core wire exposed at at least a first portion of each of the plurality of cables;
    a substrate including a core wire connection electrode electrically connecting the core wire exposed at at least the first portion of each of the plurality of cables to the substrate,
    a first fixing member fixed to a second portion of each of the plurality of cables distal to the first portion, the first fixing member covering an entire circumference of the second portion of each of the plurality of cables for holding the second portion of each of the plurality of cables at first predetermined intervals;
    a second fixing member fixed to a third portion of each of the plurality of cables proximal to the first portion, the second fixing member covering an entire circumference of the third portion of each of the plurality of cables for holding the third portion of each of the plurality of cables at second predetermined intervals;
    wherein the first fixing member and the second fixing member are separately fixed to the substrate at different positions on the substrate; and
    the core wire is fixed to the substrate at a position between the first fixing portion and the second fixing portion.

2. The cable connection structure according to claim 1, wherein the first fixing member and the second fixing member are formed of insulating resin.

3. The cable connection structure according to claim 1, wherein the cable is a coaxial cable comprising:
    the core wire,
    a dielectric covering around the core wire,
    a shield covering around the dielectric, and
    the jacket covering around the shield,
    wherein the core wire, the dielectric, and the shield are exposed stepwise in a proximal direction of each of the plurality of cables,
    the exposed core wire and the exposed shield are electrically connected respectively to the core wire connection electrode and a shield connection electrode on the substrate,
    the core wire of each of the plurality of cables is further exposed at the second portion and at the third portion of each of the plurality of cables.

4. The cable connection structure according to claim 3, wherein:
    the plurality of cables comprise a first set of cables, the shield is a first shield, the core wire is a first core wire and the connection electrode is a first connection electrode;
    the cable connection structure further comprising a second set of cables, each comprising a second core wire and a second shield;
    the first shield in the first set of cables is directly connected to the shield connection electrode;
    the second shield in the second set of cables is connected to the shield connection electrode via the first shield in the first set of cables;
    the first core wire in the first set of cables is connected to the first connection electrode;
    the second core wire in the second set of cables is connected to a second connection electrode, and
    a height of the first fixing member of the first set of cables has a height above the substrate lower than a height above the substrate of the second fixing member of the first set of cables.

5. An endoscope comprising the cable connection structure according to claim 1.

6. The cable connection structure according to claim 1, wherein
    the first fixing member includes a first surface that attaches to the substrate;
    the second fixing member includes a second surface that attaches to the substrate; and the first surface is disposed apart from the second surface in a longitudinal direction of the cables.

7. The cable connection structure according to claim 1, wherein the cable is a coaxial cable including
the core wire,
a dielectric covering around the core wire,
a shield covering around the dielectric, and
the jacket covering around the shield,
wherein the core wire, the dielectric, and the shield are exposed stepwise in a proximal direction of each of the plurality of cables,
the exposed core wire and the exposed shield are electrically connected respectively to the core wire connection electrode and a shield connection electrode on the substrate,
the dielectric of each of the plurality of cables is further exposed at the second portion and at the third portion of each of the plurality of cables.

8. The cable connection structure according to claim 7, wherein
the plurality of cables comprise a first set of cables, the shield is a first shield, the core wire is a first core wire and the connection electrode is a first connection electrode;
the cable connection structure further comprising a second set of cables, each comprising a second core wire and a second shield;
the first shield in the first set of cables is directly connected to the shield connection electrode;
the second shield in the second set of cables is connected to the shield connection electrode via the first shield in the first set of cables;
the first core wire in the first set of cables is connected to the first connection electrode;
the second core wire in the second set of cables is connected to a second connection electrode, and
a height of the first fixing member of the first set of cables has a height above the substrate lower than a height above the substrate of the second fixing member of the first set of cables.

9. The cable connection structure according to claim 1, wherein the core wire of each of the plurality of cables is further exposed at the second portion of each of the plurality of cables.

10. The cable connection structure according to claim 1, wherein the core wire of each of the plurality of cables is further exposed at the third portion of each of the plurality of cables.

11. The cable connection structure according to claim 1, wherein the cable comprises a dielectric, the dielectric of each of the plurality of cables is exposed at the second portion of each of the plurality of cables.

12. The cable connection structure according to claim 1, wherein the cable comprises a dielectric, the dielectric of each of the plurality of cables is exposed at the third portion of each of the plurality of cables.

13. A cable connection structure comprising:
a plurality of cables, each including:
a jacket; and
a core wire exposed at at least a first portion of each of the plurality of cables;
a substrate including a core wire connection electrode electrically connecting the core wire exposed at least the first portion of each of the plurality of cables to the substrate,
a first fixing member fixed to a second portion of each of the plurality of cables distal to the first portion, the first fixing member having a first hole corresponding to each of the plurality of cables for holding the second portion of each of the plurality of cables at first predetermined intervals;
a second fixing member fixed to a third portion of each of the plurality of cables proximal to the first portion, the second fixing member having a second hole corresponding to each of the plurality of cables for holding the third portion of each of the plurality of cables at second predetermined intervals;
wherein the first fixing member and the second fixing member are separately fixed to the substrate at different positions on the substrate; and
the core wire is fixed to the substrate at a position between the first fixing portion and the second fixing portion.

14. The cable connection structure according to claim 13, wherein the first fixing member and the second fixing member are formed of insulating resin and are fixed to the substrate.

15. The cable connection structure according to claim 13, wherein the cable is a coaxial cable comprising:
the core wire,
a dielectric covering around the core wire,
a shield covering around the dielectric, and
the jacket covering around the shield, wherein the core wire, the dielectric, and the shield are exposed stepwise in a proximal direction of each of the plurality of cables,
the exposed core wire and the exposed shield are electrically connected respectively to the core wire connection electrode and a shield connection electrode on the substrate, and
the core wire of each of the plurality of cables is further exposed at the second portion and at the third portion of each of the plurality of cables.

16. An endoscope comprising the cable connection structure according to claim 13.

* * * * *